(12) United States Patent
Reiffenrath et al.

(10) Patent No.: US 6,303,194 B1
(45) Date of Patent: Oct. 16, 2001

(54) ACETYLENE DERIVATIVES, AND LIQUID-CRYSTALLINE MEDIUM

(75) Inventors: Volker Reiffenrath, Rossdorf; Matthias Bremer, Darmstadt, both of (DE)

(73) Assignee: Merck Patent Gesellschaft (DE)

( * ) Notice: Subject to any disclaimer, the term of this patent is extended or adjusted under 35 U.S.C. 154(b) by 0 days.

(21) Appl. No.: 09/452,166

(22) Filed: Dec. 1, 1999

(51) Int. Cl.⁷ .......................... C09K 19/34; C09K 19/30; G02F 1/13; C07D 319/06; C07C 43/184
(52) U.S. Cl. ................ 428/1.1; 252/299.61; 252/299.63; 549/373; 549/374; 549/369; 570/188
(58) Field of Search ...................... 252/299.63, 299.61; 428/1.1; 549/369, 373, 374; 570/188; 585/534

(56) References Cited

U.S. PATENT DOCUMENTS

| | | | | |
|---|---|---|---|---|
| 4,528,114 | * | 7/1985 | Petrzilka | ............................ 252/299.6 |
| 5,961,880 | * | 10/1999 | Kirsch et al. | .................... 252/299.61 |
| 5,968,410 | * | 10/1999 | Kirsch et al. | .................... 252/299.61 |
| 6,139,773 | * | 10/2000 | Kirsch et al. | .................... 252/299.63 |

FOREIGN PATENT DOCUMENTS

19958794 * 6/2000 (DE) .

* cited by examiner

Primary Examiner—Shean C. Wu
(74) Attorney, Agent, or Firm—Millen, White, Zelano & Branigan, P.C.

(57) ABSTRACT

The invention relates to acetylene derivatives of the formula I

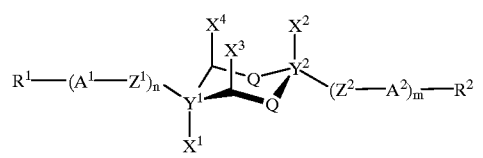

in which n, m, $R^1$, $R^2$, $X^1$, $X^2$, $X^3$, $X^4$, $Z^1$, $Z^2$, $A^1$, $A^2$, Q, $Y^1$ and $Y^2$ are as defined below, wherein at least one of the groups $X^1$, $X^2$, $X^3$ and $X^4$ is —C≡C—$R^3$, $R^3$ is H, alkyl($C_1$–$C_8$), Cl, CN, $SF_5$ or $CF_3$.

16 Claims, No Drawings

ACETYLENE DERIVATIVES, AND LIQUID-CRYSTALLINE MEDIUM

The invention relates to novel acetylene derivatives of the formula I

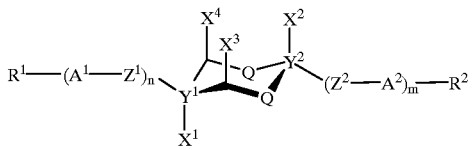

in which

R$^1$ and R$^2$, independently of one another, are H, —CN, —F, —OCHF$_2$, —OCF$_3$, —OCHFCF$_3$, —OCH$_2$CF$_3$ or —OCF$_2$—CF$_3$, an alkyl radical having 1–12 carbon atoms which is unsubstituted or at least monosubstituted by halogen or CN and in which, in addition, one or more CH$_2$ groups may each, independently of one another, be replaced by —O—, —S—, —CO—,

—CO—O—, —O—CO—, —O—CO—O— or —CH=CH— in such a way that heteroatoms are not connected directly,

X$^1$, X$^2$,

X$^3$ and X$^4$ are each, independently of one another, H or —C≡C—R$^3$ in the axial position, where at least one of the groups X$^1$, X$^2$, X$^3$ and X$^4$ is not H, R$^3$ is H, alkyl having 1 to 8 carbon atoms, Cl, CN, SF$_5$ or CF$_3$, Q is —CH$_2$— or —O—, Y$^1$ and Y$^2$, independently of one another, are C or Si, A$^1$ and A$^2$, independently of one another, are an unsubstituted or F- or CN-substituted trans-1,4-cyclohexylene radical, in which, in addition, one or more non-adjacent CH$_2$ groups may be replaced by —O— and/or —S—,

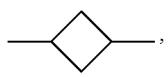

or

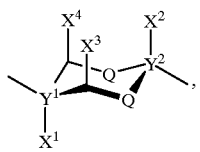

Z$^1$ and Z$^2$ are each, independently of one another, —CO—O—, —O—CO—, —CH$_2$O—, —O—, —O—CH$_2$—, —CH$_2$CH$_2$—, —CH=CH—, or a single bond, and n and m, independently of one another, are 0, 1, 2 or 3, where m+n is 1, 2, 3 or 4.

The invention also relates to the use of the compounds of the formula I as components of liquid-crystalline media, and to liquid-crystal and electro-optical display elements which contain the liquid-crystalline media according to the invention.

The compounds of the formula I frequently have a small positive or negative value of the dielectric anisotropy and can be used as components of liquid-crystalline media, in particular for displays based on the principle of the twisted cell, the guest-host effect, the effect of deformation of aligned phases (DAP) or electrically controlled birefringence (ECB) or the effect of dynamic scattering.

The substances employed hitherto for this purpose all have certain disadvantages, for example inadequate stability to the action of heat, light or electric fields, or unfavourable elastic and/or dielectric properties.

The invention had the object of finding novel, stable, liquid-crystalline or mesogenic compounds of particularly low optical anisotropy Δn and negative or positive dielectric anisotropy which are suitable as components of liquid-crystalline media, in particular for TFT amd STN displays.

It has now been found that the compounds of the formula I are eminently suitable as components of liquid-crystalline media. They can be used to obtain stable liquid-crystalline media, in particular suitable for TFT or STN displays. The novel compounds are distinguished, in particular, by high thermal stability, which is advantageous for a high "holding ratio", and exhibit favorable clearing point values. The compounds of the formula I have an optical anisotropy value Δn of <0.03, preferably <0.02, which is attributable to a particularly high value of n⊥, at a reduced temperature of 0.9 and a wavelength of 589 nm. The reduced temperature here is defined as follows:

$$\frac{\text{measurement temperature in } K}{\text{clearing point temperature in } K} = \text{reduced temperature}$$

Liquid-crystalline media having very small optical anisotropy values are of particular importance for reflective and transmissive applications, i.e. applications in which the particular LCD experiences no or only supportive background illumination. Low values of Δn are achieved by using substituents X$^1$, X$^2$, X$^3$ and/or X$^4$ having the highest possible polarizability. Owing to the small volume of the substituents X$^1$, X$^2$, X$^3$ and/or X$^4$ groups, the other LC properties, such as clearing point and viscosity, of liquid-crystal mixtures to which the compounds according to the invention are added are only impaired slightly.

The provision of compounds of the formula I very generally considerably broadens the range of liquid-crystalline substances which are suitable, from various applicational points of view, for the preparation of liquid-crystalline mixtures.

The compounds of the formula I have a broad range of applications. Depending on the choice of substituents, these compounds can serve as base materials of which liquid-crystalline media are predominantly composed; however, it is also possible to add compounds of the formula I to liquid-crystalline base materials from other classes of compound in order, for example, to modify the dielectric and/or optical anisotropy of a dielectric of this type and/or to optimize its threshold voltage and/or its viscosity. Addition of compounds of the formula I to liquid-crystalline dielectrics allows the Δn values of such media to be reduced.

The meaning of the formula I covers all isotopes of the chemical elements bound in the compounds of the formula I. In enantiomerically pure or enriched form, the compounds of the formula I are also suitable as chiral dopants and in general for producing chiral mesophases.

In the pure state, the compounds of the formula I are colorless and form liquid-crystalline mesophases in a temperature range which is favorably located for electro-optical use. They are stable chemically, thermally and to light.

The invention thus relates to the compounds of the formula I and to the use of these compounds as components of liquid-crystalline media. The invention furthermore relates to liquid-crystalline media comprising at least one compound of the formula I, and to liquid-crystal display elements, in particular electro-optical display elements, which contain media of this type.

Above and below, n, m, $R^1$, $R^2$, $R^3$, $X^1$, $X^2$, $X^3$, $X^4$, $Z^1$, $Z^2$, $A^1$, $A^2$, Q, $Y^1$ and $Y^2$ are as defined above, unless expressly stated otherwise. If the radical $X^1$ occurs more than once, it can have the same or different meanings. The same applies to all other groups which occur more than once.

For reasons of simplicity, Cyc below denotes a cyclohexane-1,4-diyl radical or a 1- or 4-silacyclohexane-1,4-diyl radical, Dio denotes a 1,3-dioxane-2,5-diyl radical, Dit denotes a 1,3-dithiane-2,5-diyl radical, and Bi denotes a bicyclo[2.2.2]octylene radical, where Cyc may be unsubstituted or mono- or polysubstituted by F or CN.

W denotes the following structural unit:

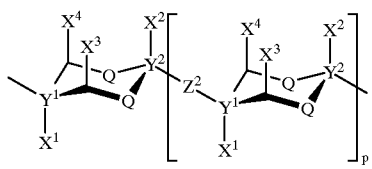

in which $X^1$, $X^2$, $X^3$, $X^4$, Q, $Y^1$, $Y^2$ and $Z^2$ are as defined above, and p is 0, 1, 2 or 3.

Preferred meanings of the group W are given by the sub-formulae W1 to W7:

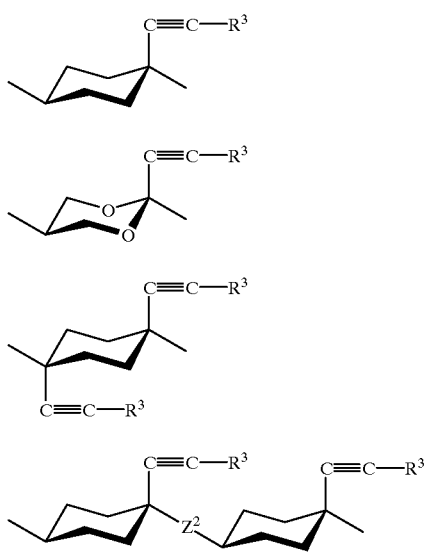

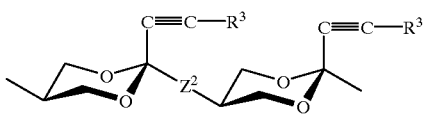

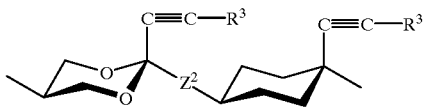

in which $Z^2$ and $R^3$ are as defined above.

The formula I covers the preferred compounds of the sub-formulae Ia1 to Ia12, which, besides the group W, contain a six-membered ring:

| | |
|---|---|
| $R^1$—W-Cyc-$R^2$ | Ia1 |
| $R^1$—W—$CH_2CH_2$-Cyc-$R^2$ | Ia2 |
| $R^1$—W—COO-Cyc-$R^2$ | Ia3 |
| $R^1$—W-Dio-$R^2$ | Ia4 |
| $R^1$—W—$CH_2CH_2$-Dio-$R^2$ | Ia5 |
| $R^1$—W—COO-Dio-$R^2$ | Ia6 |
| $R^1$-Cyc-W—$R^2$ | Ia7 |
| $R^1$-Dio-W—$R^2$ | Ia8 |
| $R^1$-Cyc-$CH_2CH_2$—W—$R^2$ | Ia9 |
| $R^1$-Dio-$CH_2CH_2$—W—$R^2$ | Ia10 |
| $R^1$-Cyc-COO—W—$R^2$ | Ia11 |
| $R^1$-Dio-COO—W—$R^2$ | Ia12 | furthermore the likewise preferred compounds of the sub-formulae Ib1 to Ib72, which, in addition to the group W, contain two six-membered rings:

| | |
|---|---|
| $R^1$-Cyc-Cyc-W-$R^2$ | Ib1 |
| $R^1$-Dio-Cyc-W-$R^2$ | Ib2 |
| $R^1$-Cyc-$CH_2CH_2$-Cyc-W-$R^2$ | Ib3 |
| $R^1$-Dio-$CH_2CH_2$-Cyc-W-$R^2$ | Ib4 |
| $R^1$-Cyc-COO-Cyc-W-$R^2$ | Ib5 |
| $R^1$-Dio-COO-Cyc-W-$R^2$ | Ib6 |
| $R^1$-Cyc-Dio-W-$R^2$ | Ib7 |
| $R^1$-Dio-Dio-W-$R^2$ | Ib8 |
| $R^1$-Cyc-$CH_2CH_2$-Dio-W-$R^2$ | Ib9 |
| $R^1$-Dio-$CH_2CH_2$-Dio-W-$R^2$ | Ib10 |
| $R^1$-Cyc-COO-Dio-W-$R^2$ | Ib11 |
| $R^1$-Dio-COO-Dio-W-$R^2$ | Ib12 |
| $R^1$-Cyc-Cyc-$CH_2CH_2$-W-$R^2$ | Ib13 |
| $R^1$-Dio-Cyc-$CH_2CH_2$-W-$R^2$ | Ib14 |
| $R^1$-Cyc-Dio-$CH_2CH_2$-W-$R^2$ | Ib15 |
| $R^1$-Dio-Dio-$CH_2CH_2$-W-$R^2$ | Ib16 |
| $R^1$-Cyc-Cyc-COO-W-$R^2$ | Ib17 |
| $R^1$-Dio-Cyc-COO-W-$R^2$ | Ib18 |
| $R^1$-Cyc-Dio-COO-W-$R^2$ | Ib19 |
| $R^1$-Dio-Dio-COO-W-$R^2$ | Ib20 |
| $R^1$-Cyc-W-Cyc-$R^2$ | Ib21 |
| $R^1$-Dio-W-Cyc-$R^2$ | Ib22 |
| $R^1$-Cyc-$CH_2CH_2$-W-Cyc-$R^2$ | Ib23 |
| $R^1$-Dio-$CH_2CH_2$-W-Cyc-$R^2$ | Ib24 |
| $R^1$-Cyc-COO-W-Cyc-$R^2$ | Ib25 |
| $R^1$-Dio-COO-W-Cyc-$R^2$ | Ib26 |
| $R^1$-Cyc-W-$CH_2CH_2$-Cyc-$R^2$ | Ib27 |
| $R^1$-Dio-W-$CH_2CH_2$-Cyc-$R^2$ | Ib28 |
| $R^1$-Cyc-W-COO-Cyc-$R^2$ | Ib29 |
| $R^1$-Dio-W-COO-Cyc-$R^2$ | Ib30 |

| | |
|---|---|
| R¹-Cyc-W-Dio-R² | Ib31 |
| R¹-Dio-W-Dio-R² | Ib32 |
| R¹-Cyc-CH₂CH₂-W-Dio-R² | Ib33 |
| R¹-Dio-CH₂CH₂-W-Dio-R² | Ib34 |
| R¹-Cyc-COO-W-Dio-R² | Ib35 |
| R¹-Dio-COO-W-Dio-R² | Ib36 |
| R¹-Cyc-W-CH₂CH₂-Dio-R² | Ib37 |
| R¹-Dio-W-CH₂CH₂-Dio-R² | Ib38 |
| R¹-Cyc-W-COO-Dio-R² | Ib39 |
| R¹-Dio-W-COO-Dio-R² | Ib40 |
| R¹-W-Cyc-Cyc-R² | Ib41 |
| R¹-W-CH₂CH₂-Cyc-Cyc-R² | Ib42 |
| R¹-W-COO-Cyc-Cyc-R² | Ib43 |
| R¹-W-Dio-Cyc-R² | Ib44 |
| R¹-W-CH₂CH₂-Dio-Cyc-R² | Ib45 |
| R¹-W-COO-Dio-Cyc-R² | Ib46 |
| R¹-W-Cyc-CH₂CH₂-Cyc-R² | Ib47 |
| R¹-W-Dio-CH₂CH₂-Cyc-R² | Ib48 |
| R¹-W-Cyc-COO-Cyc-R² | Ib49 |
| R¹-W-Dio-COO-Cyc-R² | Ib50 |
| R¹-W-Cyc-Dio-R² | Ib51 |
| R¹-W-CH₂CH₂-Cyc-Dio-R² | Ib52 |
| R¹-W-COO-Cyc-Dio-R² | Ib53 |
| R¹-W-Dio-Dio-R² | Ib54 |
| R¹-W-CH₂CH₂-Dio-Dio-R² | Ib55 |
| R¹-W-COO-Dio-Dio-R² | Ib56 |
| R¹-W-Cyc-CH₂CH₂-Dio-R² | Ib57 |
| R¹-W-Dio-CH₂CH₂-Dio-R² | Ib58 |
| R¹-W-Cyc-COO-Dio-R² | Ib59 |
| R¹-W-Dio-COO-Dio-R² | Ib60 |
| R¹-Cyc-CH₂CH₂-W-CH₂CH₂-Cyc-R² | Ib61 |
| R¹-Dio-CH₂CH₂-W-CH₂CH₂-Cyc-R² | Ib62 |
| R¹-Cyc-CH₂CH₂-W-CH₂CH₂-Dio-R² | Ib63 |
| R¹-Dio-CH₂CH₂-W-CH₂CH₂-Dio-R² | Ib64 |
| R¹-Cyc-CH₂CH₂-Cyc-CH₂CH₂-W-R² | Ib65 |
| R¹-Dio-CH₂CH₂-Cyc-CH₂CH₂-W-R² | Ib66 |
| R¹-Cyc-CH₂CH₂-Dio-CH₂CH₂-W-R² | Ib67 |
| R¹-Dio-CH₂CH₂-Dio-CH₂CH₂-W-R² | Ib68 |
| R¹-W-CH₂CH₂-Cyc-CH₂CH₂-Cyc-R² | Ib69 |
| R¹-W-CH₂CH₂-Dio-CH₂CH₂-Cyc-R² | Ib70 |
| R¹-W-CH₂CH₂-Cyc-CH₂CH₂-Dio-R² | Ib71 |
| R¹-W-CH₂CH₂-Dio-CH₂CH₂-Dio-R² | Ib72 | and the preferred compounds of the sub-formulae Ic1 to Ic55, which, in addition to the group W, contain three six-membered rings:

| | |
|---|---|
| R¹-W-Cyc-Cyc-Cyc-R² | Ic1 |
| R¹-W-CH₂CH₂-Cyc-Cyc-Cyc-R² | Ic2 |
| R¹-W-Dio-Cyc-Cyc-R² | Ic3 |
| R¹-W-CH₂CH₂-Dio-Cyc-Cyc-R² | Ic4 |
| R¹-W-Cyc-CH₂CH₂-Cyc-Cyc-R² | Ic5 |
| R¹-W-Dio-CH₂CH₂-Cyc-Cyc-R² | Ic6 |
| R¹-W-Cyc-Cyc-CH₂CH₂-Cyc-R² | Ic7 |
| R¹-W-Dio-Cyc-CH₂CH₂-Cyc-R² | Ic8 |
| R¹-W-Cyc-Dio-Cyc-R² | Ic9 |
| R¹-W-CH₂CH₂-Cyc-Dio-Cyc-R² | Ic10 |
| R¹-W-Dio-Dio-Cyc-R² | Ic11 |
| R¹-W-CH₂CH₂-Dio-Dio-Cyc-R² | Ic12 |
| R¹-W-Cyc-CH₂CH₂-Dio-Cyc-R² | Ic13 |
| R¹-W-Dio-CH₂CH₂-Dio-Cyc-R² | Ic14 |
| R¹-W-Cyc-Dio-CH₂CH₂-Cyc-R² | Ic15 |
| R¹-Cyc-Dio-CH₂CH₂-Cyc-W-R² | Ic16 |
| R¹-Dio-Dio-CH₂CH₂-Cyc-W-R² | Ic17 |
| R¹-Cyc-Cyc-Cyc-CH₂CH₂-W-R² | Ic18 |
| R¹-Dio-Cyc-Cyc-CH₂CH₂-W-R² | Ic19 |
| R¹-Cyc-Dio-Cyc-CH₂CH₂-W-R² | Ic20 |
| R¹-Dio-Dio-Cyc-CH₂CH₂-W-R² | Ic21 |
| R¹-Cyc-Cyc-Dio-W-R² | Ic22 |
| R¹-Dio-Cyc-Dio-W-R² | Ic23 |
| R¹-Cyc-CH₂CH₂-Cyc-Dio-W-R² | Ic24 |
| R¹-Dio-CH₂CH₂-Cyc-Dio-W-R² | Ic25 |
| R¹-Cyc-Dio-Dio-W-R² | Ic26 |
| R¹-Dio-Dio-Dio-W-R² | Ic27 |
| R¹-Cyc-CH₂CH₂-Dio-Dio-W-R² | Ic28 |
| R¹-Dio-CH₂CH₂-Dio-Dio-W-R² | Ic29 |
| R¹-Cyc-Cyc-CH₂CH₂-Dio-W-R² | Ic30 |
| R¹-Dio-Cyc-CH₂CH₂-Dio-W-R² | Ic31 |
| R¹-Cyc-CH₂CH₂-Dio-W-Dio-R² | Ic32 |
| R¹-Dio-CH₂CH₂-Dio-W-Dio-R² | Ic33 |
| R¹-Cyc-Cyc-CH₂CH₂-W-Dio-R² | Ic34 |
| R¹-Dio-Cyc-CH₂CH₂-W-Dio-R² | Ic35 |
| R¹-Cyc-Dio-CH₂CH₂-W-Dio-R² | Ic36 |
| R¹-Dio-Dio-CH₂CH₂-W-Dio-R² | Ic37 |
| R¹-Cyc-Cyc-W-CH₂CH₂-Dio-R² | Ic38 |
| R¹-Dio-Cyc-W-CH₂CH₂-Dio-R² | Ic39 |
| R¹-Cyc-Dio-W-CH₂CH₂-Dio-R² | Ic40 |
| R¹-Dio-Dio-W-CH₂CH₂-Dio-R² | Ic41 |
| R¹-Cyc-W-Dio-CH₂CH₂-Cyc-R² | Ic42 |
| R¹-Dio-W-Dio-CH₂CH₂-Cyc-R² | Ic43 |
| R¹-Cyc-W-Cyc-Dio-R² | Ic44 |
| R¹-Dio-W-Cyc-Dio-R² | Ic45 |
| R¹-Cyc-CH₂CH₂-W-Cyc-Dio-R² | Ic46 |
| R¹-Dio-CH₂CH₂-W-Cyc-Dio-R² | Ic47 |
| R¹-Cyc-W-CH₂CH₂-Cyc-Dio-R² | Ic48 |
| R¹-Dio-W-CH₂CH₂-Cyc-Dio-R² | Ic49 |
| R¹-Cyc-W-Cyc-CH₂CH₂-Dio-R² | Ic50 |
| R¹-Dio-W-Cyc-CH₂CH₂-Dio-R² | Ic51 |
| R¹-Cyc-W-Dio-Dio-R² | Ic52 |
| R¹-Dio-W-Dio-Dio-R² | Ic53 |
| R¹-Cyc-CH₂CH₂-W-Dio-Dio-R² | Ic54 |
| R¹-DioCH₂CH₂-W-Dio-Dio-R₂ | Ic55 | in which $R^1$, $R^2$, Cyc, Dio and W are as defined above.

Preference is given to compounds of the formula I which contain no isolated or aromatic double bonds.

$R^1$ and $R^2$ are preferably, independently of one another, —CN, F, $OCF_3$, $CF_3$, straight-chain alkyl or alkoxy having 1 to 10 carbon atoms, in particular F, $OCF_3$, alkyl or alkoxy having 1 to 7 carbon atoms.

In preferred compounds of the formula I, $X^1$, $X^2$, $X^3$ and/or $X^4$ adopt the meaning —CH≡CH, —C≡C-alkyl, —C≡C—Cl or —C≡C—CN.

In particularly preferred compounds of the formula I, $X^3$ and $X^4$ are simultaneously H.

Preference is furthermore given to compounds of the formula I in which only one of the groups $X^1$, $X^2$, $X^3$ and $X^4$ is not H.

—C≡C— alkyl is preferably —C≡C—$CH_3$ or —C≡C—$C_2H_5$, in particular —C≡C—$CH_3$.

$A^1$ and/or $A^2$ are preferably Cyc or Dio.

Preference is also given to compounds of the formula I and all sub-formulae in which $A^1$ and/or $A^2$ is cyclohexane-1,4-diyl which is mono- or disubstituted by F or CN.

$A^1$ and/or $A^2$ are preferably

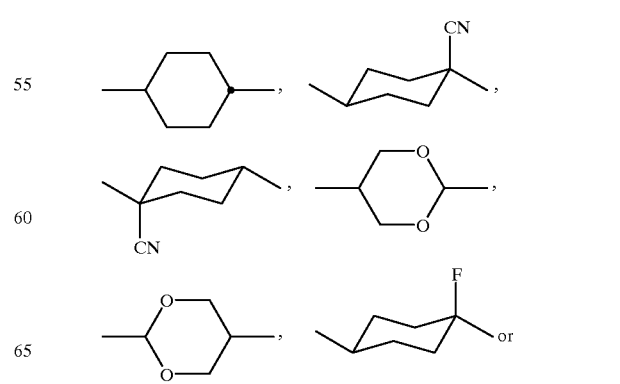

-continued

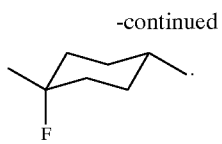

m and n are preferably 0, 1 or 2, in particular 0 or 1. m+n is preferably 1 or 2.

$Z^1$ and $Z^2$ are preferably, independently of one another, —CH$_2$CH$_2$—, —COO—, —OOC— or a single bond, particularly preferably a single bond or —CH$_2$—CH$_2$—.

Preference is given to compounds of the formula I in which $R^1$ and $R^2$ are simultaneously alkyl or alkoxy having 1 to 10 carbon atoms.

Preference is furthermore given to compounds of the formula I in which $Y^1$ and $Y^2$ are a carbon atom. Compounds of the formula I which contain not more than one dioxane ring likewise represent a preferred embodiment of the invention.

Particular preference is furthermore given to compounds of the formulae I1 to I21 from the following group:

I1
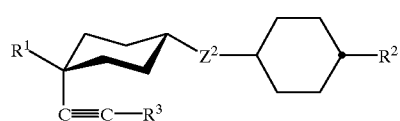

I2
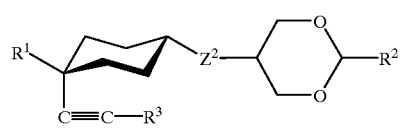

I3
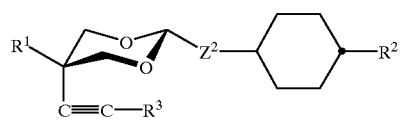

I4
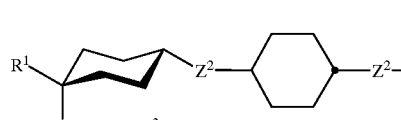

I5
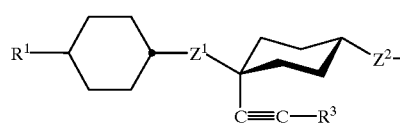

I6
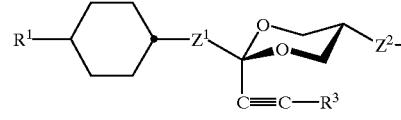

I7
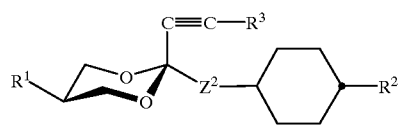

I8
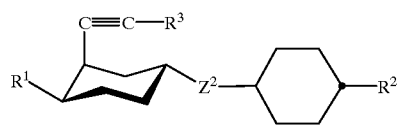

I9
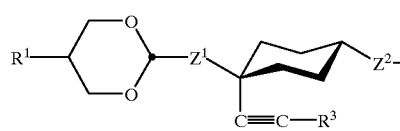

I10
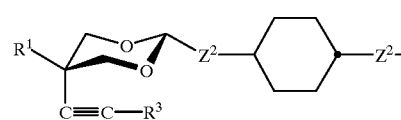

I11
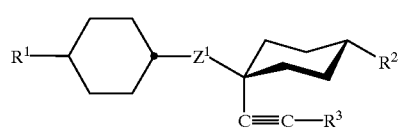

I12
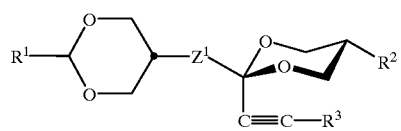

I13
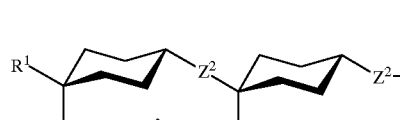

I14
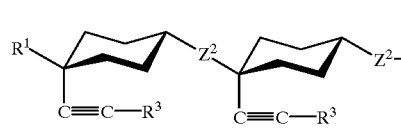

I15
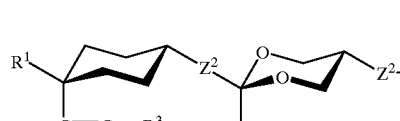

I16

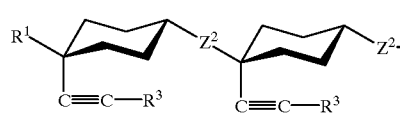

-continued

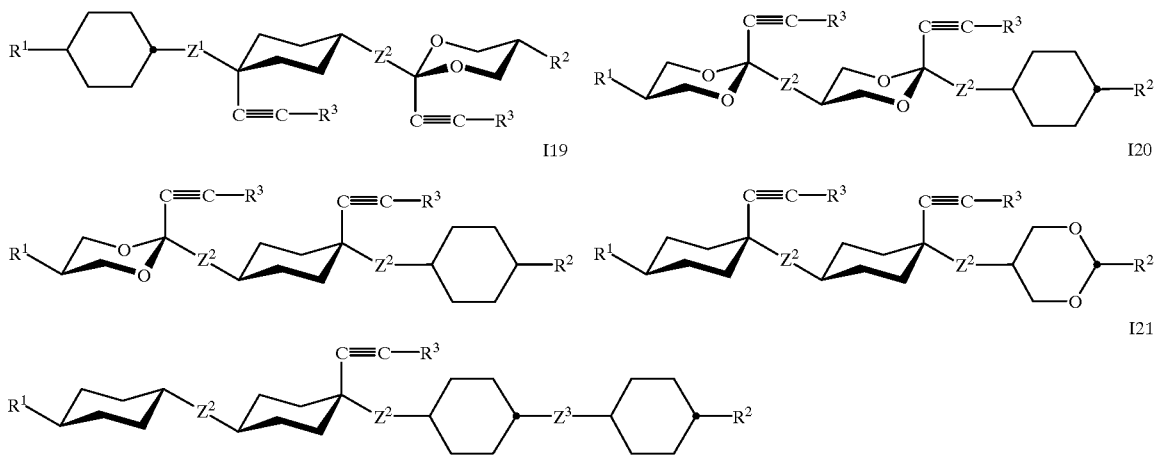

in which $R^1$, $R^2$, $R^3$, $Z^1$ and $Z^2$ are as defined above.

If $R^1$ and/or $R^2$ in the formulae above and below is an alkyl radical, this can be straight-chain or branched. It is preferably straight-chain, has 2, 3, 4, 5, 6, or 7 carbon atoms and accordingly is preferably ethyl, propyl, butyl, pentyl, hexyl or heptyl, furthermore methyl, octyl, nonyl, decyl, undecyl, dodecyl, tridecyl, tetradecyl or pentadecyl.

If $R^1$ and/or $R^2$ is an alkyl radical in which one $CH_2$ group has been replaced by —O—, this can be straight-chain or branched. It is preferably straight-chain and has 1 to 10 carbon atoms. Preferably, the first $CH_2$ group of this alkyl radical is replaced by —O—, so that the radical $R^1$ becomes alkoxy and is preferably methoxy, ethoxy, propoxy, butoxy, pentyloxy, hexyloxy, heptyloxy, octyloxy or nonyloxy.

Furthermore, one $CH_2$ group elsewhere can also be replaced by —O—, so that the radical $R^1$ and/or $R^2$ is preferably straight-chain 2-oxapropyl (=methoxy-methyl), 2- (=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl, or 2-, 3-, 4-, 5-, 6-, 7-, 8- or 9-oxadecyl.

If $R^1$ and/or $R^2$ is an alkenyl radical this can be straight-chain or branched. It is preferably straight-chain and has 2 to 10 carbon atoms. Accordingly, it is in particular vinyl, prop-1- or -2-enyl, but-1-, -2- or -3-enyl, pent-1-, -2-, -3- or -4-enyl, hex-1-, -2-, -3-, -4- or -5-enyl, hept-1-, -2-, -3-, -4-, -5- or -6-enyl, furthermore oct-1-, -2-, -3-, -4-, -5-, -6- 7-enyl, non-1-, -2-, -3-, -4-, -5-, -6-, -7- or -8-enyl, or dec-1-, -2-, -3-, -4-, -5-, -6-, -7-, -8- or -9-enyl.

$R^1$ and/or $R^2$ are particularly preferably an alkenyl radical from the following group:

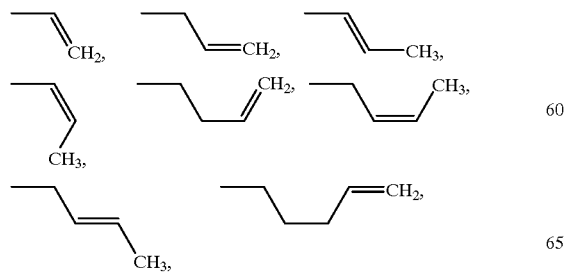

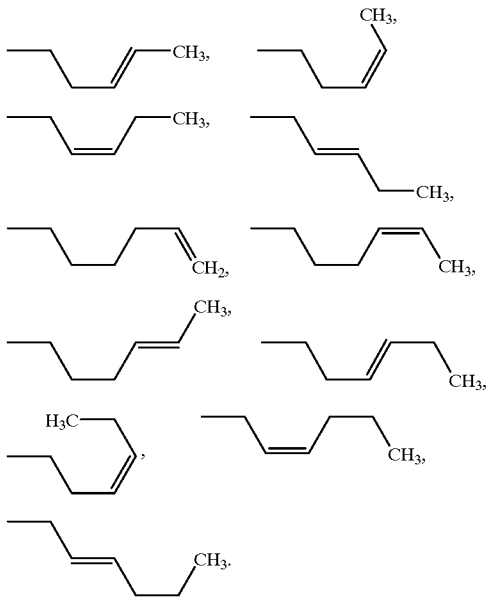

If $R^1$ and/or $R^2$ is an alkenyloxy radical, this can be straight-chain or branched. It is preferably straight-chain and has 2 to 10 carbon atoms. It is particularly preferably a radical from the following group:

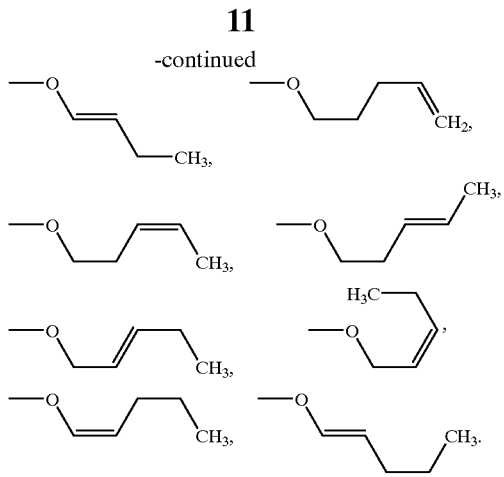

If $R^1$ and/or $R^2$ is an alkyl radical in which one $CH_2$ group has been replaced by —O— and one has been replaced by —CO—, these are preferably adjacent. These thus contain an acyloxy group —CO—O— or an oxycarbonyl group —O—CO—. These are preferably straight-chain and have 2 to 6 carbon atoms.

Accordingly, they are in particular acetoxy, propionyloxy, butyryloxy, pentanoyloxy, hexanoyloxy, acetoxymethyl, propionyloxymethyl, butyryloxymethyl, pentanoyloxymethyl, 2-acetoxyethyl, 2-propionyloxyethyl, 2-butyryloxyethyl, 3-acetoxypropyl, 3-propionyloxypropyl, 4-acetoxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl)propyl, 3-(ethoxycarbonyl)propyl or 4-(methoxycarbonyl)butyl.

If $R^1$ and/or $R^2$ is an alkyl radical which is at least monosubstituted by halogen, this radical is preferably straight-chain. Halogen is preferably F or Cl. In the case of polysubstitution, halogen is preferably F. The resultant radicals also include perfluorinated radicals. In the case of monosubstitution, the fluorine or chlorine substituent can be in any desired position, but is preferably in the ω-position.

Compounds of the formula I containing a branched wing group $R^1$ and/or $R^2$ may occasionally be of importance owing to better solubility in the customary liquid-crystalline base materials, but in particular as chiral dopants if they are optically active. Smectic compounds of this type are suitable as components of ferroelectric materials.

Branched groups of this type generally contain not more than one chain branch. Preferred branched radicals $R^1$ and/or $R^2$ are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propyl pentyl, isopropoxy, 2-methylpropoxy, 2-methylbutoxy, 3-methylbutoxy, 2-methylpentyloxy, 3-methylpentyloxy, 2-ethylhexyloxy, 1-methylhexyloxy or 1-methylheptyloxy.

Formula I covers the racemates of these compounds and the optical antipodes, and mixtures thereof.

Of these compounds of the formula I and the sub-formulae, preference is given to those in which at least one of the radicals present therein has one of the preferred meanings indicated.

Some very particularly preferred smaller groups of compounds of the formula I are those of the sub-formulae I22 to I36:

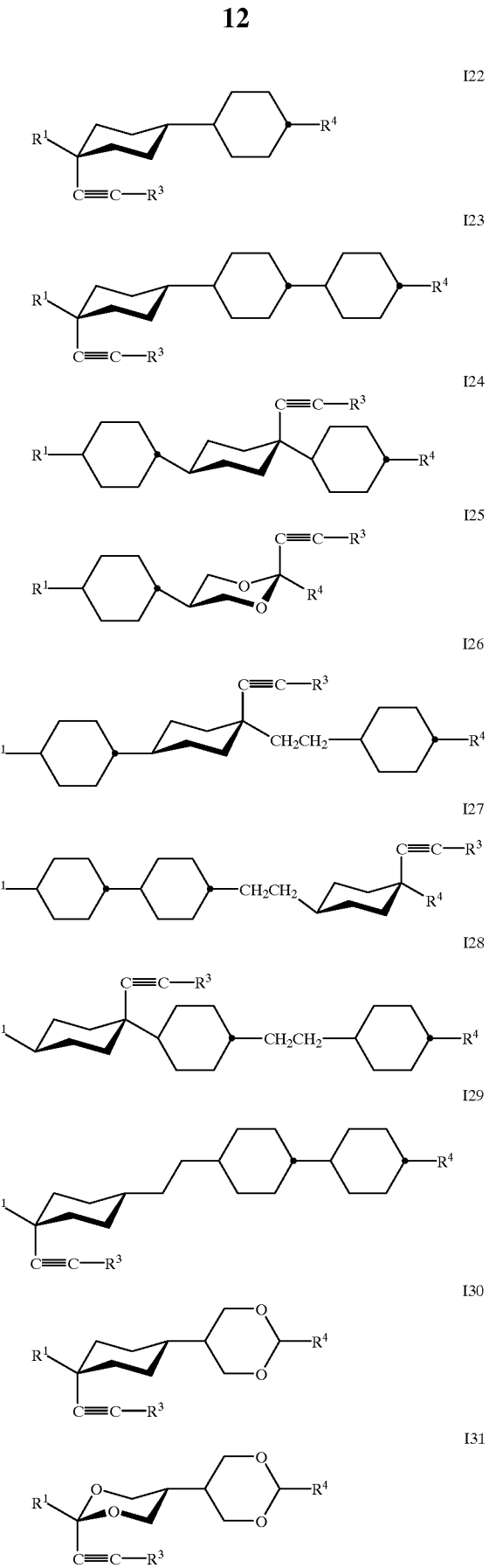

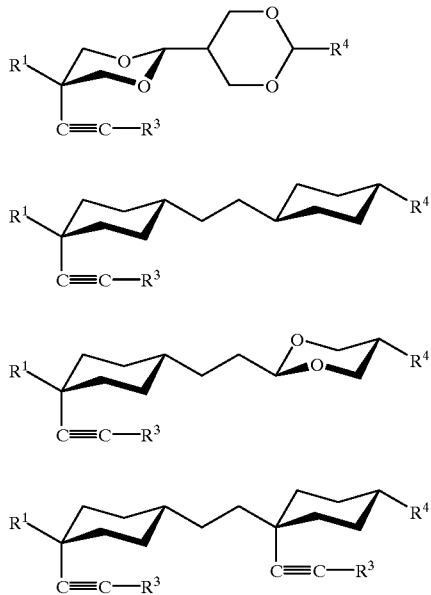

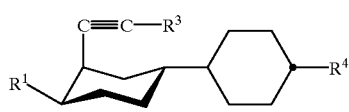

in which $R^1$ is as defined above, and $R^4$ is alkyl or alkoxy.

Very particularly preferred compounds from this group are those of the formulae I22, I23, I25, I26, I28 and I29.

The compounds of the formula I are prepared by methods known per se, as described in the literature (for example in the standard works, such as Houben-Weyl, Methoden der Organischen Chemie [Methods of Organic Chemistry], Georg-Thieme-Verlag, Stuttgart), to be precise under reaction conditions which are known and suitable for said reactions.

Use can be made here of variants which are known per se, but are not mentioned here in greater detail.

The starting materials can, if desired, also be formed in situ by not isolating them from the reaction mixture, but instead immediately converting them further into the compounds of the formula I.

The compounds of the formula I in which $A^1$ and/or $A^2$ is axially fluorinated cyclohexane can be synthesized using hydrogen fluoride under pressure or by means of amine/hydrogen fluoride adducts (for example A. V. Grosse, C. B. Linn, J. Org. Chem. 3, (1938) 26; G. A. Olah, M. Nojima, I. Kerekes, Synthesis (1973) 779); G. A. Olah, X-Y. Li, Q. Wang, G. K. S. Prakash, Synthesis (1993) 693).

The compounds according to the invention can be prepared, for example, as shown in the following reaction schemes:

Scheme 1

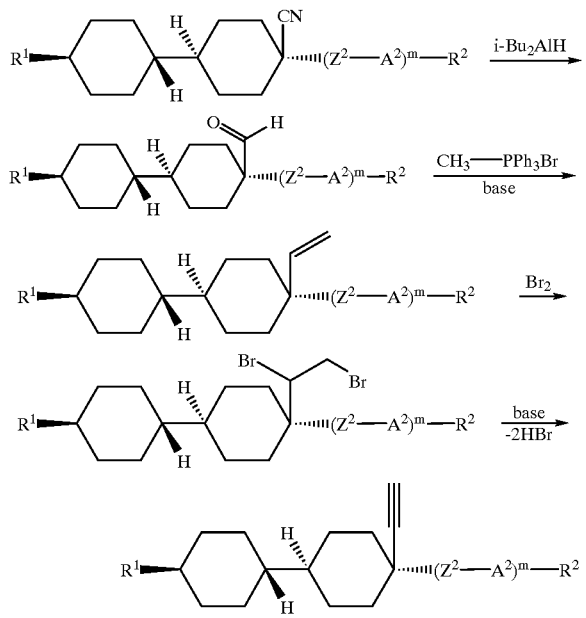

Scheme 2

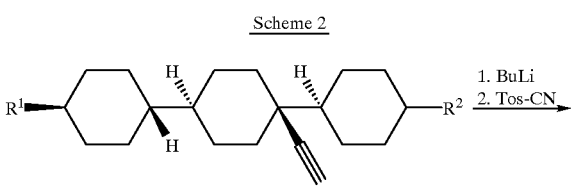

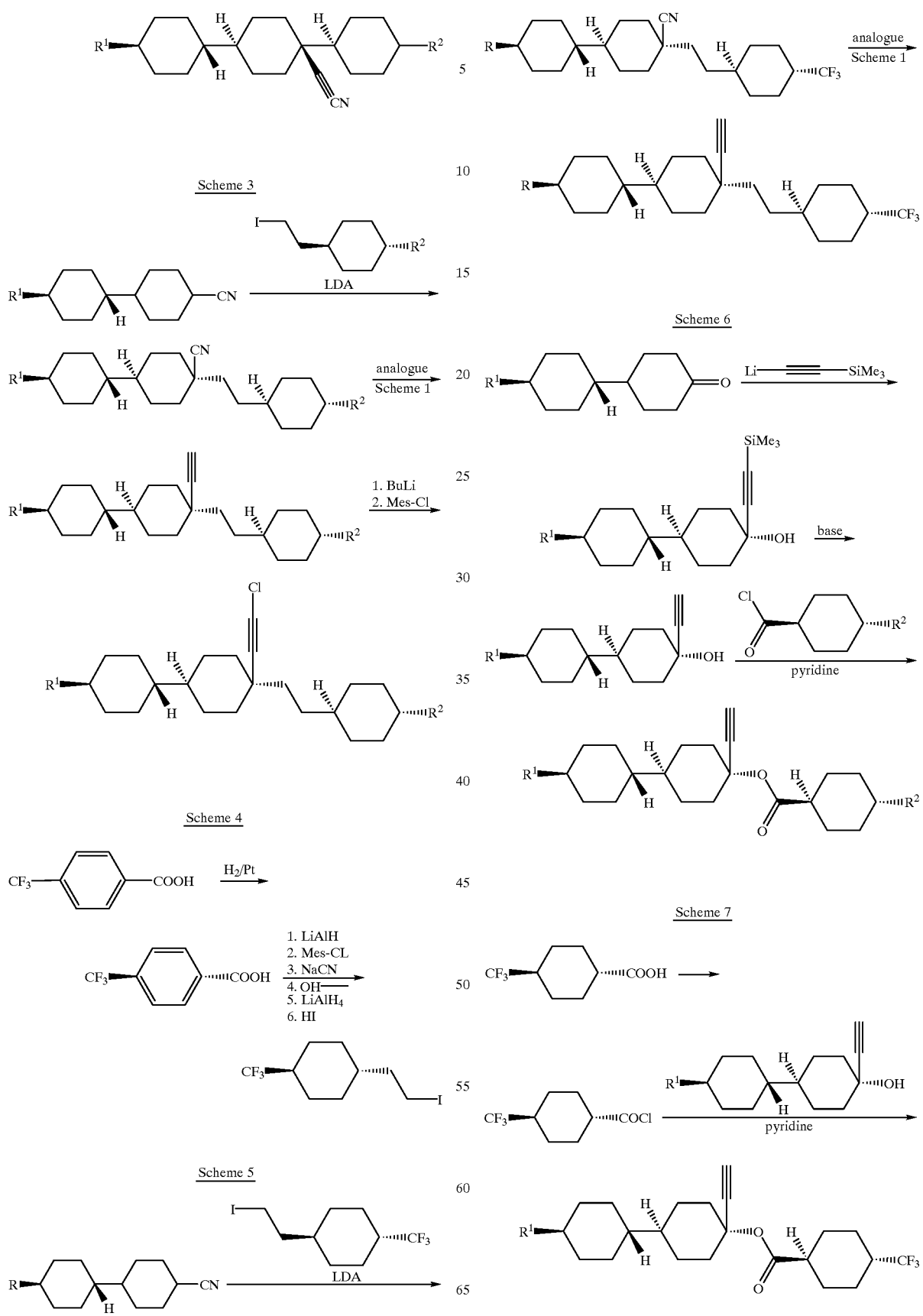

Scheme 8
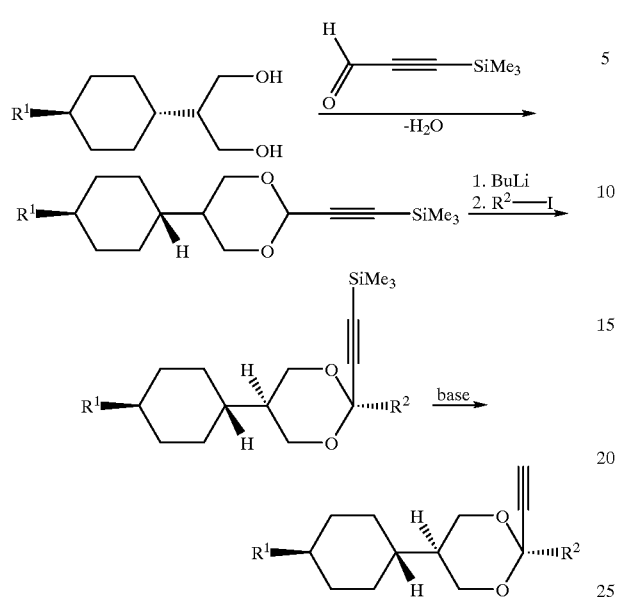
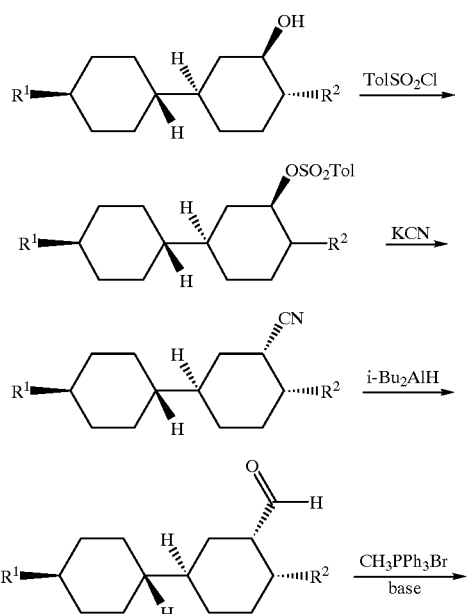
Scheme 9
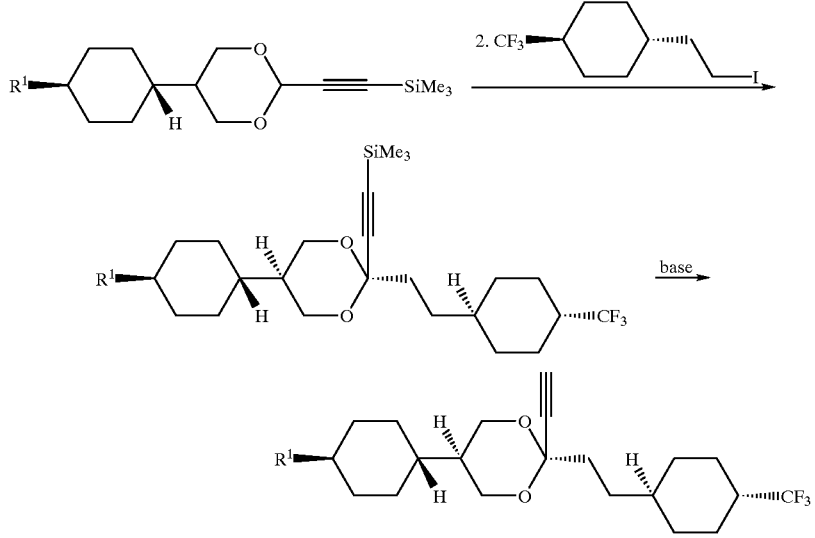
Scheme 10
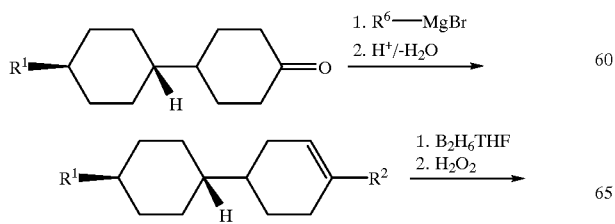
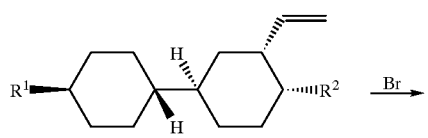

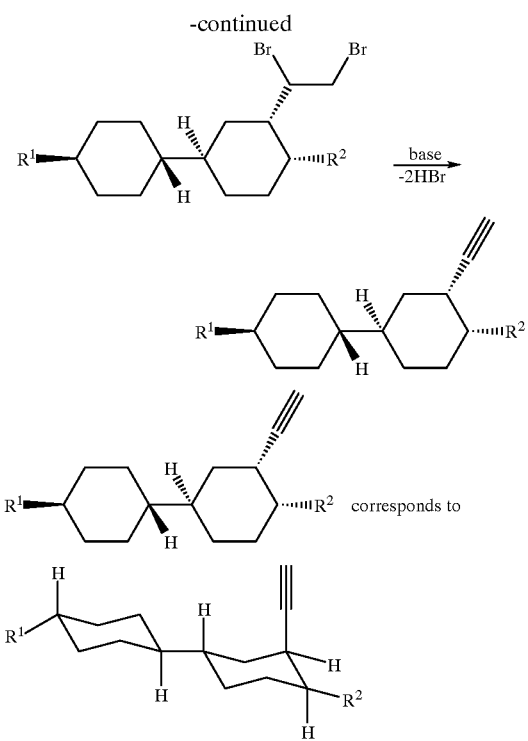

TolSO₂Cl: toluenesulphonyl chloride

Scheme 11

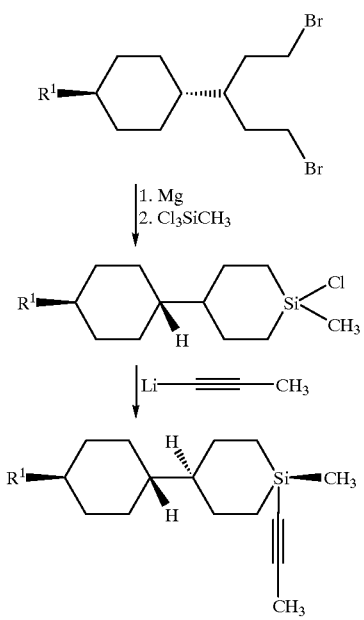

in which $R^1$ and $R^2$ are as defined above. Esters of the formula I can also be obtained by esterification of corresponding carboxylic acids (or reactive derivatives thereof) using alcohols or phenols (or reactive derivatives thereof) or by the DCC method (DCC= dicyclohexylcarbodiimide).

The corresponding carboxylic acids and alcohols or phenols are known or can be prepared analogously to known processes.

Suitable reactive derivatives of said carboxylic acids are in particular the acid halides, especially the chlorides and bromides, furthermore the anhydrides, azides or esters, in particular alkyl esters having 1–4 carbon atoms in the alkyl group.

Suitable reactive derivatives of said alcohols are in particular the corresponding metal alkoxides, preferably of an alkali metal, such as Na or K.

The esterification is advantageously carried out in the presence of an inert solvent. Particularly suitable solvents are ethers, such as diethyl ether, di-n-butyl ether, THF, dioxane or anisole, ketones, such as acetone, butanone or cyclohexanone, amides, such as DMF or hexamethylphosphoric triamide, hydrocarbons, such as benzene, toluene or xylene, halogenated hydrocarbons, such as tetrachloromethane or tetrachloroethylene, and sulfoxides, such as dimethyl sulfoxide or sulfolane. Water-immiscible solvents can at the same time advantageously be used for removal by azeotropic distillation of the water formed during the esterification. It may in some cases also be possible to use an excess of an organic base, for example pyridine, quinoline or triethylamine, as solvent for the esterification. The esterification can also be carried out in the absence of a solvent, for example by simply heating the components in the presence of sodium acetate. The reaction temperature is usually between −50° and +250°, preferably between −20° and +80°. At these temperatures, the esterification reactions are generally complete after from 15 minutes to 48 hours.

In detail, the reaction conditions for the esterification depend substantially on the nature of the starting materials used. Thus, the reaction of a free carboxylic acid with a free alcohol is generally carried out in the presence of a strong acid, for example a mineral acid, such as hydrochloric acid or sulfuric acid. A preferred reaction procedure is to react an acid anhydride or, in particular, an acid chloride with an alcohol, preferably in a basic medium, important bases being, in particular, alkali metal hydroxides, such as sodium hydroxide or potassium hydroxide, alkali metal carbonates or hydrogencarbonates, such as sodium carbonate, sodium hydrogencarbonate, potassium carbonate or potassium hydrogencarbonate, alkali metal acetates, such as sodium acetate or potassium acetate, alkaline-earth metal hydroxides, such as calcium hydroxide, or organic bases, such as triethylamine, pyridine, lutidine, collidine or quinoline. A further preferred embodiment of the esterification comprises first converting the alcohol into the sodium or potassium alkoxide, for example by treatment with ethanolic sodium hydroxide or potassium hydroxide solution, and isolating the product and reacting it with an acid anhydride or, in particular, acid chloride.

Nitriles can be obtained by replacement of halogens using copper cyanide or alkali metal cyanide.

Ethers of the formula I are obtainable by etherification of corresponding hydroxyl compounds, the hydroxyl compound advantageously first being converted into a corresponding metal derivative, for example into the corresponding alkali metal alkoxide, by treatment with NaH, NaNH₂, NaOH, KOH, Na₂CO₃ or K₂CO₃. This metal derivative can then be reacted with the appropriate alkyl halide, alkyl sulfonate or dialkyl sulfate, advantageously in an inert solvent, such as, for example, acetone, 1,2-dimethoxyethane, DMF or dimethyl sulfoxide, or alternatively with an excess of aqueous or aqueous-alcoholic NaOH or KOH, at temperatures between about 20° C. and 100° C.

The organometallic compounds are prepared, for example, by metal-halogen exchange (for example in accordance with Org. React. 6, 339–366 (1951)) between the corresponding halogen compound and an organolithium compound, such as, preferably, tert-butyl lithium or lithium naphthalenide, or by reaction with magnesium turnings.

In addition, the compounds of the formula I can be prepared by reducing a compound which contains one or more reducible groups and/or C—C bonds in place of H atoms, but otherwise conforms to the formula I.

Suitable reducible groups are preferably carbonyl groups, in particular keto groups, furthermore, for example, free or esterified hydroxyl groups or aromatically bonded halogen atoms. Preferred starting materials for the reduction are compounds which conform to the formula I, but contain a cyclohexene ring or cyclohexanone ring in place of a cyclohexane ring and/or contain a —CH=CH— group in place of a —CH$_2$CH$_2$— group and/or contain a —CO— group in place of a —CH$_2$— group and/or contain a free or functionally derived (for example in the form of its p-toluenesulfonate) OH group in place of an H atom.

The reduction can be carried out, for example, by catalytic hydrogenation at temperatures between about 0° C. and about 200° C. and at pressures between about 1 and 200 bar in an inert solvent, for example an alcohol, such as methanol, ethanol or isopropanol, an ether, such as tetrahydrofuran (THF) or dioxane, an ester, such as ethyl acetate, a carboxylic acid, such as acetic acid, or a hydrocarbon, such as cyclohexane. Suitable catalysts are advantageously noble metals, such as Pt or Pd, which may be employed in the form of oxides (for example PtO$_2$ or PdO), on a support (for example Pd on carbon, calcium carbonate or strontium carbonate) or in finely divided form.

Ketones can also be reduced by the methods of Clemmensen (using zinc, zinc amalgam or tin and hydrochloric acid, advantageously in aqueous-alcoholic solution or in the heterogeneous phase with water/toluene at temperatures between about 80 and 120° C.) or Wolff-Kishner (using hydrazine, advantageously in the presence of alkali, such as KOH or NaOH, in a high-boiling solvent, such as diethylene glycol or triethylene glycol, at temperatures between about 100 and 200° C.) to give the corresponding compounds of the formula I which contain alkyl groups and/or —CH$_2$CH$_2$— bridges.

Furthermore, reductions using complex hydrides are possible. For example, arylsulfonyloxy groups can be removed reductively using LiAlH$_4$, in particular p-toluenesulfonyloxymethyl groups can be reduced to methyl groups, advantageously in an inert solvent, such as diethyl ether or THF, at temperatures between about 0 and 100° C.

Double bonds can be hydrogenated using NaBH$_4$ or tributyltin hydride in methanol.

The starting materials are either known or can be prepared analogously to known compounds.

The liquid-crystalline media according to the invention preferably comprise from 2 to 40 components, in particular from 4 to 30 components, as further constituents besides one or more compounds according to the invention. These media very particularly preferably comprise from 7 to 25 components besides one or more compounds according to the invention. These further constituents are preferably selected from nematic or nematogenic (monotropic or isotropic) substances, in particular substances from the classes of the azoxybenzenes, benzylideneanilines, biphenyls, terphenyls, phenyl or cyclohexyl benzoates, phenyl or cyclohexyl cyclohexanecarboxylates, phenyl or cyclohexyl cyclohexylbenzoates, phenyl or cyclohexyl cyclohexylcyclohexanecarboxylates, cyclohexylphenyl benzoates, cyclohexanecarboxylates and cyclohexylcyclohexanecarboxylates, phenylcyclohexanes, cyclohexylbiphenyls, phenylcyclohexylcyclohexanes, cyclohexylcyclohexanes, cyclohexylcyclohexylcyclohexenes, 1,4-bis-cyclohexylbenzenes, 4,4'-bis-cyclohexylbiphenyls, phenyl- or cyclohexylpyrimidines, phenyl- or cyclohexylpyridines, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenylcyclohexyl)ethanes, 1-cyclohexyl-2-biphenylylethanes, 1-phenyl-2-cyclohexylphenylethanes optionally halogenated stilbenes, benzyl phenyl ethers, tolans and substituted cinnamic acids. The 1,4-phenylene groups in these compounds may also be fluorinated.

The most important compounds suitable as further constituents of media according to the invention can be characterized by the formulae 1, 2, 3, 4 and 5:

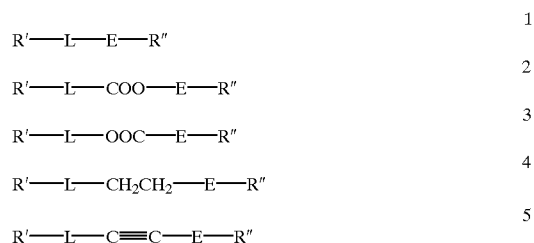

In the formulae 1, 2, 3, 4 and 5, L and E, which may be identical or different, are in each case, independently of one another, a bivalent radical from the group formed by -Phe-, -Cyc-, -Phe-Phe-, -Phe-Cyc-, -Cyc-Cyc-, -Pyr-, -Dio-, -G-Phe- and -G-Cyc- and their mirror images, where Phe is unsubstituted or fluorine-substituted 1,4-phenylene, Cyc is trans-1,4-cyclohexylene or 1,4-cyclohexylene, Pyr is pyrimidine-2,5-diyl or pyridine-2,5-diyl, Dio is 1,3-dioxane-2,5-diyl and G is 2-(trans-1,4-cyclohexyl)ethyl, pyrimidine-2,5-diyl, pyridine-2,5-diyl or 1,3-dioxane-2,5-diyl.

One of the radicals L and E is preferably Cyc, Phe or Pyr. E is preferably Cyc, Phe or Phe-Cyc. The media according to the invention preferably comprise one or more components selected from the compounds of the formulae. 1, 2, 3, 4 and 5 in which L and E are selected from the group consisting of Cyc, Phe and Pyr and simultaneously one or more components selected from the compounds of the formulae 1, 2, 3, 4 and 5 in which one of the radicals L and E is selected from the group consisting of Cyc, Phe and Pyr and the other radical is selected from the group consisting of -Phe-Phe-, -Phe-Cyc-, -Cyc-Cyc-, -G-Phe- and -G-Cyc-, and optionally one or more components selected from the compounds of the formulae 1, 2, 3, 4 and 5 in which the radicals L and E are selected from the group consisting of -Phe-Cyc-, -Cyc-Cyc-, -G-Phe- and -G-Cyc-.

In a smaller sub-group of the compounds of the formulae 1, 2, 3, 4 and 5, R' and R" are each, independently of one another, alkyl, alkenyl, alkoxy, alkoxyalkyl, alkenyloxy or alkanoyloxy having up to 8 carbon atoms. This smaller sub-group is called group A below, and the compounds are denoted by the sub-formulae 1a, 2a, 3a, 4a and 5a. In most of these compounds, R' and R" are different from one another, one of these radicals usually being alkyl, alkenyl, alkoxy or alkoxyalkyl.

In another smaller sub-group of the compounds of the formulae 1, 2, 3, 4 and 5, which is called group B, R" is —F, —Cl, —NCS or —(O)$_i$CH$_{3-(k+1)}$F$_k$Cl$_l$, where i is 0 or 1, and k and l are 1, 2 or 3; the compounds in which R" has this meaning are denoted by the sub-formulae 1b, 2b, 3b, 4b and 5b. Particular preference is given to those compounds of the sub-formulae 1b, 2b, 3b, 4b and 5b in which R" is —F, —Cl, —NCS, —CF$_3$, —OCHF$_2$ or —OCF$_3$.

In the compounds of the sub-formulae 1b, 2b, 3b, 4b and 5b, R' is as defined for the compounds of the sub-formulae 1a–5a and is preferably alkyl, alkenyl, alkoxy or alkoxyalkyl.

In a further smaller sub-group of the compounds of the formulae 1, 2, 3, 4 and 5, R" is —CN; this sub-group is called group C below, and the compounds of this sub-group are correspondingly described by sub-formulae 1c, 2c, 3c, 4c and 5c. In the compounds of the sub-formulae 1c, 2c, 3c, 4c and 5c, R' is as defined for the compounds of the sub-formulae 1a–5a and is preferably alkyl, alkoxy or alkenyl.

In addition to the preferred compounds of groups A, B and C, other compounds of the formulae 1, 2, 3, 4 and 5 having other variants of the proposed substituents are also customary. All these substances can be obtained by methods which are known from the literature or analogously thereto.

Besides compounds of the formula I according to the invention, the media according to the invention preferably comprise one or more compounds selected from group A and/or group B and/or group C. The proportions by weight of the compounds from these groups in the media according to the invention are preferably:

| | |
|---|---|
| Group A: | 0 to 90%, preferably 20 to 90%, in particular 30 to 90% |
| Group B: | 0 to 80%, preferably 10 to 80%, in particular 10 to 65% |
| Group C: | 0 to 80%, preferably 5 to 80%, in particular 5 to 50%, | the sum of the proportions by weight of the group A and/or B and/or C compounds present in the particular media according to the invention preferably being 5%–90% and in particular from 10% to 90%.

The media according to the invention preferably comprise from 1 to 40%, particularly preferably from 5 to 30%, of the compounds according to the invention. Further preferred media are those which comprise more than 40%, in particular from 45 to 90%, of compounds according to the invention. The media preferably comprise three, four or five compounds according to the invention.

The media according to the invention are prepared in a manner which is customary per se. In general, the components are dissolved in one another, advantageously at elevated temperature. By means of suitable additives, the liquid-crystalline phases can be modified in accordance with the invention in such a manner that they can be used in all types of liquid-crystal display elements which have been disclosed hitherto. Additives of this type are known to those skilled in the art and are described in detail in the literature (H. Kelker/R. Hatz, Handbook of Liquid Crystals, Verlag Chemie, Weinheim, 1980). For example, pleochroic dyes can be added for the production of coloured guest-host systems, or substances can be added to modify the dielectric anisotropy, the viscosity and/or the orientation of the nematic phases.

The examples below are intended to illustrate the invention without representing a limitation. Above and below, percentages are percent by weight. All temperatures are given in degrees Celsius. m.p. denotes melting point, cl.p.= clearing point. Furthermore, C=crystalline state, N=nematic phase, Sm=smectic phase and I=isotropic phase. The numbers between these symbols indicate the conversion temperatures. Δn denotes the optical anisotropy (589 nm, 20° C.) and Δε the dielectric anisotropy (1 kHz, 20° C.). The Δn and Δε values of the compounds according to the invention were obtained by extrapolation from liquid-crystalline mixtures consisting of 10% of the particular compound according to the invention and 90% of the commercially available liquid crystal ZLI 4792 (Merck, Darmstadt). The viscosity (mm$^2$/sec) was determined at 20° C.

"Conventional work-up" means that water is added if necessary, the mixture is extracted with methylene chloride, diethyl ether or toluene, the phases are separated, the organic phase is dried and evaporated, and the product is purified by distillation under reduced pressure or crystallization and/or chromatography.

The entire disclosure of all applications, patents and publications, cited above, and of corresponding application German application No. DE 198 55 756.6 filed Dec. 3, 1998 are hereby incorporated by reference.

The following abbreviations are used:
THF tetrahydrofuran
KOtBu potassium tert-butoxide
RT room temperature
MTB ether methyl tert-butyl ether

EXAMPLE 1

4-Ethynyl-4,4'-dipentylbicyclohexyl a) 4,4'-Dipentylbicyclohexyl-4-carbaldehyde 61.00 g of 4,4'-dipentylbicyclohexyl-4-carbonitrile (for example obtainable in accordance with EP 0107759), dissolved in the 225 ml of toluene, are slowly added dropwise to a 16.5% solution of diisobutylaluminium hydride in hexane. The reaction mixture is stirred at RT for 2 hours and subsequently poured into a mixture of ice and dilute hydrochloric acid. The resultant mixture is stirred for 1 hour, extracted with toluene and subjected to conventional work-up, giving 4,4'-dipentylbicyclohexyl-4-carbaldehyde.

b) 4,4'-Dipentyl-4-vinylbicyclohexyl

A solution of 17.84 g of KOtBu in 100 ml of THF is added dropwise at 0C to a suspension of 53.20 g of 4,4,'-dipentylbicyclohexyl-4-carbaldehyde and 56.80 g of methyltriphenylphosphonium bromide in 300 ml of THF. The mixture is stirred at RT overnight, water is added, and the mixture is extracted with MTB ether. The combined organic phases are subjected to conventional work-up, giving 4,4'-dipentyl-4-vinylbicyclohexyl.

c) 4-(1,2-Dibromomethyl)-4,4'-dipentylbicyclohexyl 4.754 ml of bromine are added dropwise at from 0° C. to −10° C. to 36.40 g of 4,4'-dipentyl-4-vinylbicyclohexyl in 120 ml of diethyl ether. After 1 hour without cooling, water is added to the reaction mixture, which is subjected to conventional work-up, giving 4-(1,2-dibromoethyl)-4,4'-dipentylbicyclohexyl.

d) 4-Ethynyl-4,4'-dipentylbicyclohexyl 32.48 g of KOtBu are added at RT to 47.50 g of 4-(1,2-dibromoethyl)-4,4'-dipentylbicyclohexyl in 150 ml of tert-butanol. The mixture is heated to 60° C. and stirred at this temperature overnight. Water is subsequently added to the reaction mixture, which is acidified with dilute hydrochloric acid and subjected to conventional work-up, giving 4-ethynyl-4,4'-dipentylbicyclohexyl (C 16 N 35 I, Δε−1.96, Δn 0.021).

EXAMPLE 2

9.66 ml of a 15% solution of n-butyllithium in hexane are added dropwise at −70° C. to 4.80 g of 4-ethynyl-4,4'-dipentylbicyclohexyl in 40 ml of THF, and the mixture is stirred for 15 minutes. A solution of 0.99 ml of iodomethane and 1.914 ml of 1,3-dimethyltetrahydro-2-pyrimidinone in 10 ml of THF is subsequently added dropwise to the reaction solution at this temperature, and the cooling is removed. Conventional work-up gives 4,4'-dipentyl-4-prop-1-ynylbicyclohexyl (C 35 N 35.4 I, Δε−1.54, Δn 0.01).

EXAMPLE 3

9.66 ml of a 15% solution of n-butyllithium in hexane are added dropwise at −70° C. to 4.80 g of 4-ethynyl-4,4'-dipentylbicyclohexyl in 40 ml of THF, and the mixture is stirred for 15 minutes. A solution of 2.49 g of p-toluenesulfonyl cyanide in 10 ml of THF is subsequently added dropwise to the reaction solution at this temperature, and the cooling is removed. Conventional work-up gives (4,4'-dipentylbicyclohexyl-4-yl)propionitrile (C 55 I, Δε−7.98, Δn−0.022).

EXAMPLE 4

4-Ethynyl-4-methoxy-4'-propylbicyclohexyl a) 4-Ethynyl-4'-propylbicyclohexyl-4-ol 24.32 ml of (trimethylsilyl)acetylene are added dropwise at −30° C. to a solution of 30.0 g of 4'-propylbicyclohexyl-4-one and 3.41 g of tetrabutylammonium fluoride trihydrate in 300 ml of THF. The cooling bath is removed after 5 minutes, and the reaction mixture is stirred at RT for 2 hours. A suspension of 39.2 g of potassium fluoride in methanol is subsequently added, and the mixture is stirred at RT for 3 days. Conventional work-up gives 4-ethynyl-4'-propylbicyclohexyl-4-ol.

b) 4-Ethynyl-4-methoxy-4'-propylbicyclohexyl 28.85 ml of a 15% solution of butyllithium in hexane are added dropwise to a solution, cooled to −30° C., of 13.0 g of 4-ethynyl-4'-propylbicyclohexyl-4-ol in 24 ml of THF. A solution of 4.67 ml of iodomethane in 36 ml of dimethyl sulfoxide is subsequently added dropwise to the reaction mixture at −5° C. The mixture is stirred at RT overnight and subjected to conventional work-up, giving 4-ethynyl-4-methoxy-4'-propylbicyclohexyl (C 45 I, Δε−3.72, Δn−0.022).

The following compounds according to the invention are obtained analogously using the corresponding precursors:

EXAMPLES 5–22

$R^1$—$(A^1$—$Z^1)_n$—[cyclohexyl with $X^1$, $X^2$]—$R^2$

| | $R^1$ | $(A^1$—$Z^1)_n$ | $X^2$ | $X^1$ | $R^2$ |
|---|---|---|---|---|---|
| (5) | n-Pentyloxy | cyclohexyl | —C≡CH | H | n-Propyl |
| (6) | n-Propyl | dioxane | —C≡C—CH$_3$ | H | OCF$_3$ |
| (7) | n-Pentyl | bicyclohexyl | —C≡CH | H | CF$_3$ |
| (8) | Ethoxy | cyclohexyl-CH$_2$CH$_2$-cyclohexyl | —C≡C—CF$_3$ | H | F |
| (9) | n-Pentyl | dioxane-cyclohexyl | —C≡C—CN | H | n-Pentyloxy |

-continued

R¹—(A¹—Z¹)ₙ—[cyclohexane with X² and R² on one carbon, X¹ on opposite]

| R¹ | (A¹—Z¹)ₙ | X² | X¹ | R² |
|---|---|---|---|---|
| (10) n-Pentyl | —[cyclohexane]—[cyclohexane]—[cyclohexane]— | —C≡C—CH₃ | H | CF₃CF₃ |
| (11) H | —[cyclohexane]— | —C≡CH | H | n-Propyl |
| (12) Pentyloxy | —[cyclohexane]— | —C≡C—CF₃ | H | CHFCF₃ |
| (13) n-Pentyl | —[cyclohexane]— | H | —C≡C—CF₃ | n-Propyl |
| (14) n-Propyl | —[cyclohexane]—[cyclohexane]—CH₂CH₂— | H | —C≡CH | n-Propyl |
| (15) n-Propyl | —[1,3-dioxane]— | H | —C≡C—CF₃ | n-Propyl |
| (16) n-Propyl | —[cyclohexane]—[cyclohexane]— | H | —C≡CH | n-Propyl |
| (17) Ethoxy | —[cyclohexane]—CH₂CH₂—[cyclohexane]— | —C≡C—CH₃ | —C≡C—CH₃ | Methyl |
| (18) Hexyloxy | —[1,3-dioxane]—[cyclohexane]— | H | —C≡C—CF₃ | n-Propyloxy |
| (19) n-Pentyl | —[cyclohexane]—[cyclohexane]—[cyclohexane]— | —C≡CH | —C≡CH | n-Propyloxy |
| (20) n-Propyl | —[cyclohexane]— | H | —C≡C—CH₃ | n-Propyl |
| (21) n-Pentyloxy | —[cyclohexane]—[cyclohexane]—CH₂CH₂— | H | —C≡C—CF₃ | Methyl |

-continued
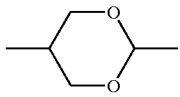
| $R^1$ | $(A^1-Z^1)_n$ | $X^2$ | $X^1$ | $R^2$ |
|---|---|---|---|---|
| (22) n-Pentyl |  | H | —C≡CH | n-Pentyl |
EXAMPLES 23–32
| $R^1$ | $(Z^2-A^2)_n$ | $X^1$ | $X^2$ | $R^2$ |
|---|---|---|---|---|
| (23) n-Propyl | 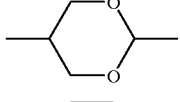 | —CH≡C—CN | H | $CHFCF_3$ |
| (24) n-Pentyloxy | 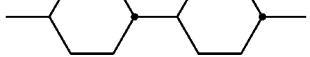 | —C≡C—Cl | H | n-Propyl |
| (25) n-Propyl | 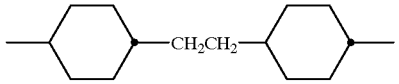 | —C≡C—$CF_3$ | H | $OCF_3$ |
| (26) n-Pentyl | 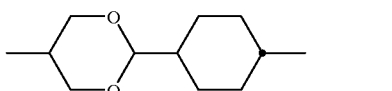 | —C≡CH | H | $CF_3$ |
| (27) Ethoxy | 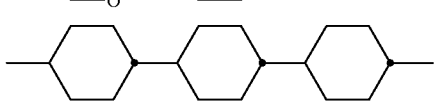 | —C≡CH | H | F |
| (28) n-Hexyloxy |  | —C≡C—Cl | H | n-Propyloxy |
| (29) n-Pentyl |  | —C≡C—$CH_3$ | H | $CF_2CF_3$ |
| (30) n-Propyl | | —C≡C—CN | H | n-Propyl |
| (31) n-Pentyloxy | | —C≡C—$SF_5$ | H | $CHFCF_3$ |
| (32) n-Propyl | | —C≡C—Cl | H | $OCF_3$ |

EXAMPLE 33

4.00 g of 4-(dimethylamino)pyridine are added to a solution of 16.00 g of 4-ethynyl-4'-propylbicyclohexyl-4-ol and 11.51 g of 4-propylcyclohexanecarboxylic acid in 120 ml of dichloromethane. 9.66 g of N,N-dicyclohexylcarbodiimide in 30 ml of methylene chloride are subsequently added dropwise at RT, and the mixture is stirred overnight. Conventional work-up gives 4-ethynyl-4'-propylbicyclohexyl-4-yl 4-propylcyclohexane-carboxylate (C 59 N 120 I, Δε −1.57, Δn 0.04).

EXAMPLE 34

5.10 ml of a 26% solution of lithium diisopropylamide in THF are added dropwise at −70° C. to 4.00 g of 4-ethynyl-4'-propylbicyclohexyl-4-yl 4-propylcyclohexanecarboxylate in 30 ml of THF, and the mixture is stirred for 15 minutes. A solution of 1.89 g of p-toluenesulfonyl cyanide in 10 ml of THF is subsequently added dropwise to the reaction solution at this temperature, and the cooling is removed. Conventional work-up gives 4-cyanoethynyl-4'-propylbicyclohexyl-4-yl 4-propylcyclohexanecarboxylate (C 89 N (58) I, Δε −10.18, Δn 0.02).

The following compounds according to the invention are obtained analogously using the corresponding precursors:

EXAMPLES 35–54

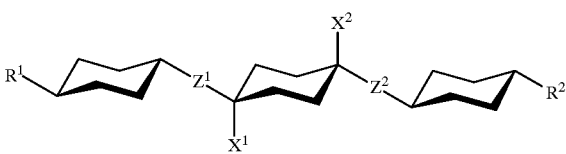

| | R¹ | Z¹ | Z² | X¹ | X² | R² | |
|---|---|---|---|---|---|---|---|
| (35) | n-Pentyloxy | — | — | —C≡CH | H | CHFCF₃ | |
| (36) | n-Propyl | — | — | —C≡C—CN | H | n-Propyl | |
| (37) | n-Propyl | —CH₂CH₂— | — | —C≡C—CF₃ | H | n-Propyl | |
| (38) | n-Propyl | — | —COO— | —C≡C—CH₃ | H | CF₃ | |
| (39) | n-Propyl | —CH₂CH₂— | —CH₂CH₂— | —C≡CH | —C≡C—Cl | n-Propyl | |
| (40) | n-Hexyloxy | —CH₂CH₂— | — | —C≡C—CN | H | n-Propyloxy | |
| (41) | n-Pentyl | — | — | —C≡C—Cl | H | CF₂CF₃ | |
| (42) | n-Propyl | — | — | —C≡C—CN | —C≡C—SF₅ | n-Propyl | |
| (43) | n-Pentyloxy | — | — | —C≡CH | H | CHFCF₃ | |
| (44) | n-Propyl | —OOC— | — | —C≡C—CH₃ | H | OCF₃ | |
| (45) | n-Propyl | —OOC— | —CH₂CH₂— | H | —C≡C—CF₃ | CHFCF₃ | |
| (46) | n-Pentyloxy | — | — | H | —C≡CH | n-Pentyl | |
| (47) | n-Propyl | — | —OOC— | H | —C≡C—CH₃ | n-Propyl | (C 69 N 951, Δz- 0.95, Δn 0.03) |
| (48) | n-Pentyl | —CH₂CH₂— | — | H | —C≡C—SF₅ | n-Propyl | |
| (49) | Ethoxy | — | — | H | —C≡C—CH₃ | Methyl | |
| (50) | n-Hexyloxy | — | —CH₂CH₂— | H | —C≡C—CN | n-Propyloxy | |
| (51) | n-Pentyl | — | — | H | —C≡C—Cl | n-Propyloxy | |
| (52) | n-Propyl | — | —CH₂CH₂— | H | —C≡CH | n-Propyl | |
| (53) | n-Pentyloxy | —OOC— | — | H | —C≡C—CN | Methyl | |
| (54) | n-Pentyl | — | — | H | —C≡C—CH₃ | n-Pentyl | |

EXAMPLES 55–74

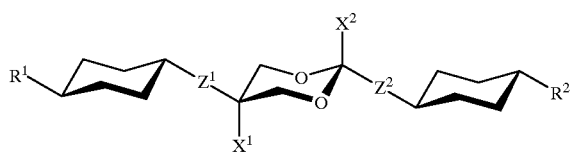

| | R¹ | Z¹ | Z² | X¹ | X² | R² |
|---|---|---|---|---|---|---|
| (55) | n-Pentyloxy | — | — | —C≡CH | H | CHFCF₃ |
| (56) | n-Pentyloxy | — | — | —C≡C—Cl | | n-Propyl |
| (57) | n-Propyl | — | —CH₂CH₂— | —C≡C—Cl | —C≡C—Cl | OCF₃ |
| (58) | n-Pentyl | — | —COO— | —C≡CH | H | CF₃ |
| (59) | Ethoxy | —CH₂CH₂— | —CH₂CH₂— | —C≡C—SF₅ | H | F |
| (60) | n-Hexyloxy | —CH₂CH₂— | — | —C≡C—Cl | H | n-Propyloxy |

-continued

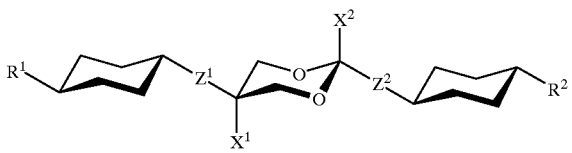

| R¹ | Z¹ | Z² | X¹ | X² | R² |
|---|---|---|---|---|---|
| (61) n-Pentyl | — | — | —C≡C—CF₃ | —C≡C—CF₃ | CF₂CF₃ |
| (62) n-Propyl | — | — | —C≡CH | H | n-Propyl |
| (63) n-Pentyloxy | — | — | —C≡C—CN | H | CHFCF₃ |
| (64) n-Propyl | — | —OOC— | —C≡C—SF₅ | H | OCF₃ |
| (65) n-Propyl | —OOC— | —CH₂CH₂— | H | —C≡C—CH₃ | CHFCF₃ |
| (66) n-Pentyloxy | — | — | —C≡C—CN | —C≡C—CN | n-Pentyl |
| (67) n-Propyl | — | — | H | —C≡CH | n-Propyl |
| (68) n-Pentyl | —CH₂CH₂— | — | H | —C≡C—Cl | n-Propyl |
| (69) Ethoxy | — | — | —C≡C—SF₅ | —C≡C—SF₅ | Methyl |
| (70) n-Hexyloxy | — | —CH₂CH₂— | H | —C≡C—Cl | n-Propyloxy |
| (71) n-Pentyl | — | — | H | —C≡C—CN | n-Propyloxy |
| (72) n-Propyl | —CH₂CH₂— | — | H | —C≡C—SF₅ | n-Propyl |
| (73) n-Pentyloxy | —OOC— | — | H | —C≡CH | Methyl |
| (74) n-Pentyl | — | — | h | —C≡C—Cl | n-Pentyl |

EXAMPLE 75

4,4'-Bis(4"-propylcyclahexanecarboxy)-4,4'-diethynylbicyclohexyl a) 4,4'-Diethynylbicyclohexyl-4,4'-diol 30.00 g of bicyclohexyl-4,4'-dione and 3.89 g of tetrabutylammonium fluoride trihydrate are dissolved in 350 ml of THF, and 30.33 g of trimethylsiylacetylene are added dropwise at RT. The reaction mixture is stirred for 2 days, a suspension of 44.86 g of potassium fluoride in 160 ml of methanol is subsequently added, and the mixture is stirred for a further 3 days. Conventional work-up gives 4,4'-diethynylbicyclohexyl-4,4'-diol.

b) 4,4'-Bis(4"-propylcyclohexanecarboxy)-4,4'-diethynylbicyclohexyl 37.5 g of 4,4'-diethynylbicyclohexyl-4,4'-diol and 51.83 g of 4-propylhexanecarboxylic acid are dissolved in 400 ml of dichloromethane, and 37.19 g of 4-(dimethylamino)pyridine are added. A solution of 78.52 g of N,N-dicyclohexylcarbodiimide in 300 ml of dichloromethane is subsequently added dropwise, and the mixture is stirred overnight. Conventional work-up gives 4,4'-bis(4"-propylcyclohexanecarboxy)-4,4'-diethynylbicyclohexyl (C 158 N 176 I).

The following compounds according to the invention are obtained analogously using the corresponding precursors:

EXAMPLES 76–85

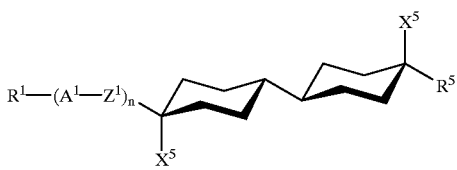

| R¹ | (A²—Z¹)ₙ | X⁵ | R⁵ |
|---|---|---|---|
| (76) n-Propyl | —⟨cyclohexyl⟩—COO— | —C≡C—CN | —OOC—⟨cyclohexyl⟩—n-Propyl |
| (77) n-Pentyloxy | —⟨cyclohexyl⟩—COO— | —C≡C—CH₃ | n-Propyloxy |
| (78) n-Propyloxy | — | —C≡C—CF₃ | OCF₃ |
| (79) n-Pentyl | —⟨cyclohexyl⟩—⟨cyclohexyl⟩—COO— | —C≡C—SF₅ | OCH₃ |

-continued $R^1-(A^1-Z^1)_n-$[cyclohexyl]$-$[cyclohexyl]$(X^5)(X^5)-R^5$

| $R^1$ | $(A^2-Z^1)_n$ | $X^5$ | $R^5$ |
|---|---|---|---|
| (80) Ethyl | —[cyclohexyl]—CH$_2$O— | —C≡CH | n-Propyloxy |
| (81) n-Hexyl | —[cyclohexyl]—COO— | —C≡C—CN | —OOC—[cyclohexyl]—Methyl |
| (82) n-Pentyloxy | — | —C≡C—Cl | OCF$_2$CF$_3$ |
| (83) n-Propyl | —[cyclohexyl]—COO— | —C≡C—SF$_5$ | n-Pentyloxy |
| (84) n-Butyl | —[cyclohexyl]—COO— | —C≡C—CN | OCF=CF$_2$ |
| (85) n-Propyloxy | — | —C≡CH | OCF$_3$ |

The following compounds according to invention are obtained analogously to the preceding Examples:

EXAMPLES 86–93

$R^1-(A^1-Z^1)_n-$[cyclohexyl]$-$[cyclohexyl]$(X^2)(X^2)-R^2$

| $R^1$ | $(A^1-Z^1)_n$ | $X^2$ | $R^2$ |
|---|---|---|---|
| (86) n-Propyl | —[cyclohexyl]— | —C≡C—CN | CHFCF$_3$ |
| (87) n-Pentyloxy | —[cyclohexyl]— | —C≡C—SF$_5$ | n-Propyl |
| (88) n-Propyl | —[dioxanyl]— | —C≡C—CH$_3$ | OCF$_3$ |
| (89) Ethoxy | —[cyclohexyl]—CH$_2$CH$_2$—[cyclohexyl]— | —C≡CH | F |

-continued
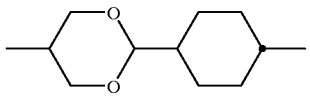
| $R^1$ | $(A^1-Z^1)_n$ | $X^2$ | $R^2$ |
|---|---|---|---|
| (90) n-Hexyloxy |  | —C≡C—CN | n-Propyloxy |
| (91) n-Propyl |  | —C≡C—CF$_3$ | n-Propyl |
| (92) n-Pentyloxy | 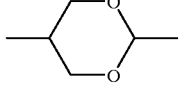 | —C≡CH | CHFCF$_3$ |
| (93) n-Propyl |  | —C≡C—CH$_3$ | OCF$_3$ |
EXAMPLES 94–100
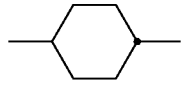
| $R^1$ | $(A^1-Z^1)_n$ | $X^1$ | $X^2$ | $R^2$ |
|---|---|---|---|---|
| (94) n-Propyl | 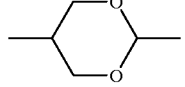 | —C≡C—SF$_5$ | H | CHFCF$_3$ |
| (95) n-Pentyloxy | | —C≡C—CN | —C≡C—CN | n-Propyl |
| (96) n-Propyl | 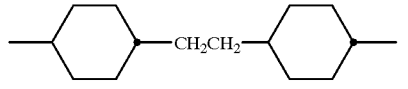 | —C≡CH | H | OCF$_3$ |
| (97) Ethoxy | —CH$_2$CH$_2$— | —C≡C—Cl | H | F |
| (98) n-Hexyloxy | 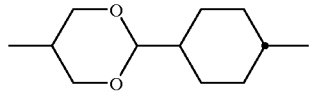 | —C≡C—CN | —C≡C—CN | n-Propyloxy |

-continued
| R¹ | (A¹—Z¹)ₙ | X¹ | X² | R² |
|---|---|---|---|---|
| (99) n-Pentyl |  | —C≡C—CH₃ | H | n-Propyl |
| (100) n-Propyloxy |  | —C≡C—Cl | H | CHFCF₃ |
EXAMPLES 101–107
| R¹ | (A¹—Z¹)ₙ | X² | R² |
|---|---|---|---|
| (101) n-Propyl | 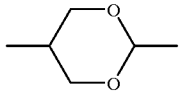 | —C≡C—CN | CHFCF₃ |
| (102) n-Pentyloxy | 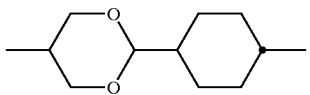 | —C≡CH | n-Propyl |
| (103) n-Propyl |  | —C≡C—Cl | OCF₃ |
| (104) n-Hexyloxy |  | —C≡C—CF₃ | n-Propyloxy |
| (105) n-Propyl | | —C≡C—SF₅ | n-Propyl |
| (106) n-Pentyloxy | | —C≡CH | CHFCF₃ |
| (107) n-Propyl | 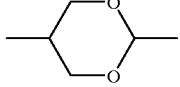 | —C≡C—CH₃ | OCF₃ |

EXAMPLES 108–115

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. Acetylene derivatives of the formula I

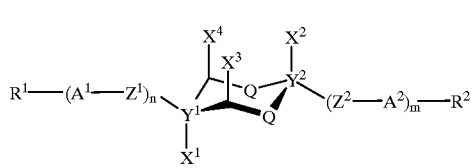

in which $R^1$ and $R^2$, independently of one another, are H, —CN, —F, —OCHF$_2$, —OCF$_3$, —OCHFCF$_3$, —OCH$_2$CF$_3$, —OCF$_2$—CF$_3$, an alkyl radical having 1–12 carbon atoms which is unsubstituted, or an alkyl radical having 1–12 carbon atoms which is substituted one or more times by substituents selected from the group consisting of halogen and CN, and in which, in addition, one or more non-adjacent CH$_2$ groups may each, independently of one another, be replaced by —O—, —S—, —CO—,

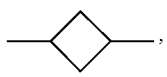

—CO—O—, —O—CO—, —O—CO—O— or —CH=CH— in such a way that heteroatoms are not connected directly, $X^1$, $X^2$, X³ and X⁴ are each, independently of one another, H or —C≡C—R³ in the axial position, where at least one of the groups X¹, X², X³ and X⁴ is not H, R³ is H, alkyl having 1 to 8 carbon atoms, Cl, CN, SF₅ or CF₃, Q is —CH₂— or —O—, Y¹ and Y², independently of one another, are C or Si, A¹ and A², independently of one another, are an unsubstituted trans-1,4-cyclohexylene radical, F-substututed trans-1-4-cyclohexylene radical or CN-substituted trans-1,4-cyclohexylene radical, in which, in addition, one or more non-adjacent CH₂ groups may be replaced by —O— and/or —S—

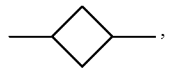

or

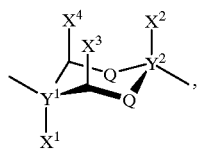

Z¹ and Z₂ are each, independently of one another, —CO—O—, —O—CO—, —CH₂O—, —O—, —O—CH₂—, —CH₂CH₂—, —CH=CH—, or a single bond, and n and m, independently of one another, are 0, 1, 2 or 3, where m+n is 1, 2, 3 or 4.

2. Acetylene derivatives of the formula I according to claim 1, characterized in that they have a value for the optical anisotropy Δn of <0.03 at a reduced temperature of 0.9 and a wavelength of 589 nm.

3. Acetylene derivatives of the formula I according to claim 1, characterized in that Y¹ and Y² are C.

4. Acetylene derivatives of the formula I according to claim 1, characterized in that m and n are 0, 1 or 2.

5. Acetylene derivatives of the formula I according to claim 1, characterized in that Z¹ and Z², independently of one another, are —CH₂CH₂—, —COO—, —OOC— or a single bond.

6. Acetylene derivatives of the formula I according to claim 1, characterized in that R¹ and R² are simultaneously alkyl or alkoxy having 1 to 10 carbon atoms.

7. Acetylene derivatives of the formula I according to claim 5, characterized in that R¹ and R² are simultaneously alkyl or alkoxy having 1 to 10 carbon atoms.

8. Acetylene derivatives of the formula I according to claim 1, characterized in that X¹, X², X³, and/or X⁴ has the meaning —C≡CH, —C≡C-alkyl, —C≡C—Cl or —C≡C—CN.

9. Acetylene derivatives of the formula I according to claim 6, characterized in that X¹, X², X³, and/or X⁴ has the meaning —C≡CH, —C≡C-alkyl, —C≡C—Cl or —C≡C—CN.

10. Acetylene derivatives of the formula I according to claim 1, characterized in that X³ and X⁴ are simultaneously H.

11. Acetylene derivatives of the formula I according to claim 7, characterized in that X³ and X⁴ are simultaneously H.

12. A method of using compounds of the formula I according to claim 1 which comprises incorporating a compound of formula I of claim 1 as a component of a liquid-crystalline medium.

13. Liquid-crystalline medium having at least two liquid-crystalline components, which comprises at least one compound of the formula I of claim 1.

14. Liquid-crystal display element, which contains a liquid-crystalline medium according to claim 13.

15. Reflective or transflective liquid-crystal display element, which contains, as dielectric, a liquid-crystalline medium according to claim 13.

16. Electro-optical display element, which contains, as dielectric, a liquid-crystalline medium according to claim 13.

* * * * *

UNITED STATES PATENT AND TRADEMARK OFFICE
CERTIFICATE OF CORRECTION

PATENT NO.     : 6,303,194 B1
DATED          : October 16, 2001
INVENTOR(S)    : Reiffenrath et al.

Page 1 of 1

It is certified that error appears in the above-identified patent and that said Letters Patent is hereby corrected as shown below:

<u>Title page,</u>
Item [63], insert the following:
-- Foreign Application Priority Data
Dec. 3, 1998     (DE) ........................198 55 756.6 --

Signed and Sealed this

Twentieth Day of August, 2002

Attest:

JAMES E. ROGAN
Attesting Officer      *Director of the United States Patent and Trademark Office*